(12) United States Patent
Kelly et al.

(10) Patent No.: US 6,255,302 B1
(45) Date of Patent: Jul. 3, 2001

(54) 1,4-PIPERAZINE DERIVATIVES

(75) Inventors: Michael G. Kelly, Newbury Park, CA (US); Yvette L. Palmer, Yardley, PA (US)

(73) Assignee: American Home Products Corporation, Madison, NJ (US)

(*) Notice: Subject to any disclaimer, the term of this patent is extended or adjusted under 35 U.S.C. 154(b) by 0 days.

(21) Appl. No.: 09/459,793

(22) Filed: Dec. 13, 1999

Related U.S. Application Data

(60) Provisional application No. 60/150,702, filed on Dec. 17, 1998.

(51) Int. Cl.[7] .................. C07D 401/06; C07D 401/14; C07D 403/06; A61K 31/496; A61P 25/24

(52) U.S. Cl. .................. 514/217.05; 514/252.18; 514/253.09; 514/253.11; 514/254.01; 514/254.09; 514/295; 540/598; 544/295; 544/360; 544/364; 544/372

(58) Field of Search .................. 544/360, 295, 544/364, 372; 514/252.18, 253.09, 253.11, 217.05, 254.09, 254.01; 540/598

(56) References Cited

U.S. PATENT DOCUMENTS

| 4,977,159 | 12/1990 | Sevrin et al. | 514/292 |
|---|---|---|---|
| 5,162,523 | 11/1992 | Keith et al. | 540/227 |
| 5,192,775 | 3/1993 | Malen et al. | 514/321 |

FOREIGN PATENT DOCUMENTS

| 409081 A1 | * | 1/1991 | (EP). |
| 445026 A1 | * | 9/1991 | (EP). |
| 9906395 | * | 2/1999 | (WO). |

OTHER PUBLICATIONS

DiStefano, Peter S., in "Annual Reports in Medicinal Chemistry, vol 28", 1993, Academic Press, San Diego, p11–17.*
Shiosaki, K. et al, in "Annual Reports in Medicinal Chemistry, vol. 30", 1995, Academic Press, San Diego, p31–40.*
Hershenson, F.M. et al, in "Annual Reports in Medicinal Chemistry, vol. 19", 1984, Academic Press, San Diego, p19–40.*
Miranda, R.C. et al, in "Annual Reports in Medicinal Chemistry, vo. 31", 1996, Academic Press, San Diego, p11–20.*
Annual Reports in Medicinal Chemistry, vol. 27, James Bristol, ed., Academic Press, San Diego, 1992, p 21–25.*
Developments in the Treatment of Parkinson's Disease, no author listed, Drug Ther. Bull., 37(5) 1999, 36–40.*
Saxena, P.R., Serotonin Receptors: Subtypes, Functional Responses and Therapeutic Relevance. Pharmac. Ther. Voil. 66, 339–368 (1995).

* cited by examiner

Primary Examiner—Mukund J. Shah
Assistant Examiner—Thomas McKenzie
(74) Attorney, Agent, or Firm—Rebecca R. Barrett

(57) ABSTRACT

Compounds of the formula

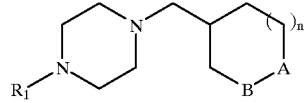

A are useful for the treatment of disorder of the central nervous system including anxiety, depression, panic, alcohol and drug addiction, sexual dysfunction, sleep disorders, cognitive disorders, Alzheimer's disease and Parkinson's disease.

14 Claims, No Drawings

1,4-PIPERAZINE DERIVATIVES

This application claims the benefit of U.S. Provisional Application No. 60/150,702, filed Dec. 17, 1998.

BACKGROUND OF THE INVENTION

U.S. Pat. No. 4,977,159 describes 2-[(4-piperidyl)methyl]-1,2,3,4-tetrahydro-9H-pyrido[3,4-B]indole derivatives and their application in treating depressive state, anxiety state or hypertension.

DESCRIPTION OF THE INVENTION

This invention relates to novel arylpiperidine derivatives. In accordance with this invention are provided novel arylpiperadine derivatives which are agonists and antagonists of the 5HT1A receptor subtype. By virtue of their high binding affinity to the 5HT1A receptor, compounds of the present invention are useful for the treatment of central nervous system (CNS) disorders such as depression, anxiety, panic, OCD, sleep disorders, sexual dysfunction, alcohol and drug addiction, cognition enhancement, Alzheimer's disease, Parkinson's disease, obesity and migraine.

Compounds of the present invention are represented by the general formula

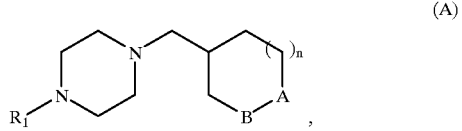

(A)

in which:
R1 is aryl or heteroaryl;
A is NR2 or CH2 and B is N, NR2 or CH2, provided that A is not equal to B;
R2 is hydrogen, alkyl, cycloalkyl, alkylcycloalkyl, heterocycloalkyl, alkylhetero-cycloalkyl, aryl, aralkyl, heteroaryl, alkylheteroaryl or COR3;
R3 is hydrogen, alkyl, cycloalkyl, heterocycloalkyl, aryl or heteroaryl;
n is an integer from 0 to 2, or a pharmaceutical salt thereof.
In some preferred embodiments of the present invention R1 is phenyl; 2-, 3- or 4-pyridyl; 2-pyrimidyl; benzodioxan-5-yl; indol-4-yl; 3-thienyl; 1-, or 2-naphthyl. In still more preferred embodiments RI is phenyl or indol-4-yl.
In some preferred embodiments of the present invention R2 is aralkyl, alkylheterocycloalkyl or COR3.

"Alkyl" as used herein means a branched or straight chain having from 1 to 6 carbon atoms and more preferably from 1 to 4 carbon atoms. Exemplary alkyl groups include methyl, ethyl, propyl, isopropyl, butyl, isobutyl, t-butyl, pentyl and hexyl. Lower alkyl refers to alkyl having from 1 to 6 carbon atoms.

"Alkoxy" as used herein means an alkyl-O group in which the alkyl group is as previously described. Exemplary alkoxy groups include methoxy, ethoxy, n-propoxy, i-propoxy, n-butoxy, and t-butoxy.

"Aryl" as used herein means mono or bicyclic aromatic ring having from 6 to 10 carbon atoms. Monocyclic rings preferably have 6 members and bicyclic rings preferably have 8, 9 or 10 membered ring structures. Exemplary aryl groups include phenyl, naphthyl, and biphenyl. In some preferred embodiments aryl is phenyl, 1-naphthyl or 2-naphthyl. In still more preferred embodiments aryl is phenyl. The aryl group may be substituted with one or more substituents. Substituted aryl groups preferably have one to three substituents.

"Cycloalkyl" as used herein means a monocyclic alkyl group having from 3 to 8 carbon atoms. In some preferred embodiments cycloalkyl may be substituted with from 1 to 3 substituents.

"Heterocycloalkyl" as used herein means a monocyclic alkyl group having from 3 to 8 members containing one or more, and preferably one or two, heteroatoms selected from N and O. Exemplary heterocycloalkyl groups include piperidinyl, piperazinyl and morpholino. In some embodiments heterocycloalkyl groups may be substituted with from 1 to 3 substituents.

Halogen, as used herein means fluorine, chlorine, iodine and bromine.

"Heteroaryl" means 5 to 10 membered mono or bicyclic aromatic ring having from 1 to 3 heteroatoms selected from N, O and S. Monocyclic rings preferably have 5 or 6 members and bicyclic rings preferably have 8, 9 or 10 membered ring structures. Exemplary heteroaryls include pyrrolyl, furyl, thienyl, imidazolyl, pyrazolyl, oxazolyl, isoxazolyl, thiazolyl, isothiazolyl, pyridyl, pyrazinyl, pyrimidinyl, indolyl, quinolyl, isoquinolyl, benzopyranyl and benzodioxanyl. Preferred heteroaryl groups include thienyl, pyridyl, furyl, indolyl and benzodioxanyl. More preferred are heteroaryl groups including 2-thienyl, 3-thienyl, 2-pyridyl, 3-pyridyl, 4-pyridyl, 2-furyl, 3-furyl, 3-indolyl, indol-4-yl and benzodiox-5-yl. The heteroaryl group may be substituted with one or more substituents. Substituted heteroaryl groups preferably have from 1 to 3 substituents.

Suitable substituents, unless otherwise noted, include halogen, alkyl, hydroxy, alkoxy, amino, amido, nitro, alkylamino, alkylamido, perhaloalkyl, carboxyalkyl, carboxy, carbamide, dialkylamino and aryl.

Carbon number refers to the number of carbons in the carbon backbone and does not include carbon atoms occurring in substituents such as an alkyl or alkoxy substituents.

Where terms are used in combination, the definition for each individual part of the combination applies unless defined otherwise. For instance, alkylcycloalkyl is an alkyl-cycloalkyl group in which alkyl and cycloalkyl are as previously described.

Pharmaceutically acceptable salts are the acid addition salts which can be formed from a compound of the above general formula and a pharmaceutically acceptable acid such as phosphoric, sulfuric, hydrochloric, hydrobromic, citric, maleic, succinic, fumaric, acetic, lactic, nitric, sulfonic, p-toluene sulfonic, methane sulfonic acid, and the like.

The compounds of this invention contain a chiral center, providing for various seteroisomeric forms of the compounds such as racemic mixtures as well as the individual optical isomers. The individual isomers can be prepared directly or by asymmetric or stereospecific synthesis or by conventional separation of optical isomers from the racemic mixture.

Compounds of the present invention may be prepared by those skilled in the art of organic synthesis employing conventional methods which utilize readily available reagents and starting materials.

For example, condensation of an aryl substituted piperazine with a suitably protected nipecotic acid or isonipecotic acid derivative provides the amides shown in scheme A and scheme B below. The reaction may be conducted in the presence of activating reagents such as 1-(3- dimethylaminopropyl)-3-ethylcarbodiimide hydro-chloride (DAEC), 1-hydroxybenzotriazole hydrate (HOBT) and 4-methylmorpholine (NMM).

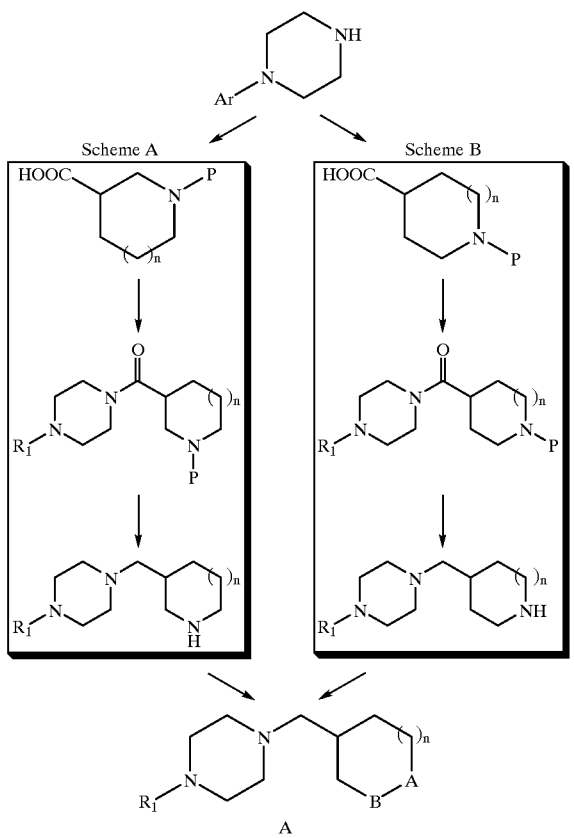

A tert-butyl carbamate is an example of a suitable protection group (P) which can be removed by the action of acid. Deprotection to the amine, and subsequent reduction of the amide using lithium aluminum hydride or borane-tetrahydrofuran complex can afford the required unsubstituted product A. The product may be alkylated with alkyl halides under the influence of a base such as sodium hydride or potassium carbonate to afford further derivatives, or alternatively may be acylated with carboxylic acid derivatives and the amide subsequently reduced under the above noted conditions to afford further derivatives.

The following non-limiting specific examples are included to illustrate the synthetic procedures used for preparing compounds of the formula A. In these examples, all chemicals and intermediates are either commercially available or can be prepared by standard procedures found in the literature or are known to those skilled in the art of organic synthesis. Several preferred embodiments are described to illustrate the invention. However, it should be understood that the invention is not intended to be limited to the specific embodiments.

Intermediate 1

N-tert-Butoxycarbonyl-(1-(2-methoxy-phenyl)-piperazine)-4-isonipecotamide 4-(2-Methoxyphenyl)piperazine hydrochloride (5.0 g, 21.8 mmol) was added to a mixture of DAEC (4.18 g, 21.8 mmol), HOBT (1.3 equivalents, 3.83 g, 28.3 mmol) and N-t-butoxycarbonyl isonipecotic acid (5 g, 21.8 mmol) in DMF (35 mL), and the resulting solution was treated with NMM (2.5 equivalents, 6.0 mL, 54.5 mmol) and stirred at 0° C. for 16 hours. Water (100 mL) was added, the product extracted into ethyl acetate (3×50 mL) and the combined organics were washed with IN-HCl (20 mL), saturated $NaHCO_3$ (25 mL) and dried over anhydrous sodium sulfate. Filtration and concentration in vacuum afforded the product as a white solid (8.79 g, 99% yield)

Elemental Analysis for: $C_{22}H_{33}N_3O_4$ Calculated: C, 65.48; H. 8.24; N, 10.41 Found: C, 65.23; H, 8.15; N, 10.23

Intermediate 2

1-(2-Methoxy-phenyl)-piperazine)-4-isonipecotamide

The carbamate from intermediate 1 (8.79 g, 21.8 mmol) was dissolved in 4M-HCl dioxan (40 mL) and the solution stirred at ambient temperature for 6 hours. The mixture was concentrated in vacuum, diethyl ether (50(mL) added and the precipitated product collected by filtration and washed with ether (50 mL) to afford a white solid (7.28 g, 98% yield)

Elemental Analysis for: $C_{17}H_{26}N_3O_2$ Calculated: C, 60.08; H, 7.71; N, 10.43 Found: C, 59.99; H. 7.56; N, 10.23

Intermediate 3

N-tert-Butoxycarbonyl-(1-(2-methoxy-phenyl)-piperazine)-4-nipecotamide 4-(2-Methoxyphenyl)piperazine hydrochloride (5.0 g, 21.8 mmol) was added to a mixture of DAEC (4.18 g, 21.8 mmol), HOBT (1.3 equivalents, 3.83 g, 28.3 mmol) and N-t-butoxycarbonyl nipecotic acid (5 g, 21.8 mmol) in DMF (35 mL), and the resulting solution was treated with NMM (2.5 equivalents, 6.0 mL, 54.5 mmol) and stirred at 0° C. for 16 hours. Water (100 mL) was added, the product extracted into ethyl acetate (3×50 mL) and the combined organics were washed with 1N-HCl (20 mL), saturated $NaHCO_3$ (25 mL) and dried over anhydrous sodium sulfate. Filtration and concentration in vacuum afforded the product as a white solid (8.79 g, 99% yield)

Elemental Analysis for: $C_{22}H_{33}N_3O_4$ Calculated: C, 65.48; H, 8.24; N, 10.41 Found: C, 65.45; H, 8.23; N, 10.32

Intermediate 4

(1-(2-methoxy-phenyl)-piperazine)-4-nipecotamide

The carbamate from intermediate 3 (8.79 g, 21.8 mmol) was dissolved in 4M-HCl dioxan (40 mL) and the solution stirred at ambient temperature for 6 hours. The mixture was concentrated in vacuum, diethyl ether (50(mL) added and the precipitated product collected by filtration and washed with ether (50 mL) to afford a white solid (7.28 g, 98% yield)

Elemental Analysis for: $C_{17}H_{26}N_3O_2$ Calculated: C, 60.08; H, 7.71; N, 10.43 Found: C, 60.22; H, 7.56; N, 10.39

Example 1

1-(2-Methoxy-phenyl)-4-piperidin-4-ylmethyl-piperazine

A solution of the amide from intermediate 2 (7.28 g, 21.8 mmol) and triethylamine (6 mL) in THF (100 mL) was treated with the dropwise addition of borane-THF (1.0 M, 76 mL) at 0° C. under nitrogen. The mixture was refluxed for 16 hours and after cooling to 0° C., the reaction was terminated by the addition of 2N-HCl (50 mL). After stirring for 1 hour, the solution was made basic with NaOH and the product extracted into ethyl acetate (3×35 mL). The combined organics were washed with water (50 mL), brine (50 mL) and dried over anhydrous sodium sulfate. Filtration and concentration in vacuum gave the required product (4.4 g, 78% yield). An ethanolic solution of the product was treated with a hot ethanolic solution of fumaric acid (1.0 equivalents) and afforded the fumarate salt of the titled compound as a light yellow colored solid.

$M^+$=289

Elemental Analysis for: $C_{17}H_{27}N_3O$ $1.0C_4H_4O_4$ $1.1H_2O$ Calculated: C, 59.30; H, 7.87; N, 9.88 Found: C, 58.80; H, 7.63; N, 10.34

Example 2

Cyclohexyl-{4-[4-(2-methoxy-phenyl)-piperazin-1-ylmethyl]-piperidin-1-yl}-methanone Cyclohexanecarbonyl chloride (0.506 g, 3.5 mmol) was added to a solution of 1-(2-methoxyphenyl)-4-piperidin-4-ylmethyl-piperazine (1.0 g, 3.5 mmol) from example 1 and triethylamine (2 equivalents, 1 mL) in $CH_2Cl_2$ (30 mL) and the solution stirred under $N_2$ at 0° C. for 16 hours. The mixture was concentrated under vacuum, water (50 mL) added and the product extracted into ethyl acetate (3×25 mL). The combined organics were washed with water (25 mL), saturated sodium bicarbonate (20mL) and brine (25 mL). After drying over sodium sulfate, filtration and concentration under vacuum afforded the titled product (0.765 g, 55% yield). An ethanolic solution of the product was treated with a hot ethanolic solution of fumaric acid (1.0 equivalents) and afforded the fumarate salt of the titled compound as a light yellow colored solid.

$M^+$=399

Elemental Analysis for: $C_{24}H_{37}N_3O_2$, $1.0C_4H_4O_4$ Calculated: C, 65.22; H, 8.01; N, 8.15 Found: C, 65.00; H, 8.19; N, 8.18

Example 3

1-(1-Cyclohexylmethyl-piperidin-3-ylmethyl)-4-(2-methoxy-phenyl)-piperazine

Borane-THF (1.0M, 4 mmol) was added dropwise to a THF solution of 1-(2-methoxy phenyl)-4-piperidin-4-ylmethyl-piperazine (0.382 g, 0.957 mmol) from example 1 at 0° C. under nitrogen. The mixture was refluxed for 16 hours and after cooling to 0° C., the reaction was terminated by the addition of 2N-HCl (50 mL). After stirring for 1 hour, the solution was made basic with NaOH and the product extracted into ethyl acetate (3×35 mL). The combined organics were washed with water (50 mL), brine (50 mL) and dried over anhydrous sodium sulfate. Filtration and concentration in vacuum gave the required product (0.19 g, 51% yield). An ethanolic solution of the product was treated with a hot ethanolic solution of fumaric acid (2.0 equivalents) and afforded the fumarate salt of the titled compound as a light yellow colored solid.

$M^+$=385

Elemental Analysis for: $C_{24}H_{39}N_3O1.0C_4H_4O_4$ Calculated: C, 62.22; H, 7.67; N, 6.80 Found: C, 62.25; H, 7.50; N. 6.92

Example 4

{4-[4-(2-Methoxy-phenyl)-piperazin-1-ylmethyl]-piperidin-1-yl}-phenyl-methanone

Benzoyl chloride (0.49 g, 3.5 mmol) was added to a solution of 1-(2-methoxyphenyl)-4-piperidin-4-ylmethyl-piperazine (1.0 g, 3.5 mmol) from example 1 and triethylamine (2 equivalents, 1 mL) in $CH_2Cl_2$ (30 mL) and the solution stirred under $N_2$ at 0° C. for 16 hours. The mixture was concentrated under vacuum, water (50 mL) added and the product extracted into ethyl acetate (3×25 mL). The combined organics were washed with water (25 mL), saturated sodium bicarbonate (20 mL) and brine (25 mL). After drying over sodium sulfate, filtration and concentration under vacuum afforded the titled product (0.91 g, 66% yield). An ethanolic solution of the product was treated with a hot ethanolic solution of fumaric acid (1.0 equivalents) and afforded the fumarate salt of the titled compound as a light yellow colored solid.

$M^+$=393

Elemental Analysis for: $C_{24}H_{31}N_3O_2$ $1.0C_4H_4O_4$ Calculated: C, 65.99; H, 6.92; N, 8.25 Found: C, 66.17; H, 6.91; N, 8.30

Example 5

1-(1-Benzyl-piperidin-4-ylmethyl)-4-(2-methoxy-phenyl)-piperazine 4-(2-Methoxyphenyl)piperazine hydrochloride (1.0 g, 4.35 mmol) was added to a mixture of DAEC (0.83 g, 4.35 mmol), HOBT (1.5 equivalents, 0.88 g) and N-benzoylisonipecotic acid (1 g, 4.35 mmol) in DMF (15 mL), and the resulting solution was treated with NMM (2.5 equivalents, 1.2 mL) and stirred at 0° C. for 16 hours. Water (50 mL) was added, the product extracted into ethyl acetate (3×50 mL) and the combined organics were washed with 1N-HCl (10 mL), saturated NaHCO3(15 mL) and dried over anhydrous sodium sulfate. Filtration and concentration in vacuum afforded the required amide product as a white solid (1.77 88% yield).

$M^+$=407

Elemental Analysis for: $C_{24}H_{29}N_3O_3$ Calculated: C, 70.74; H. 7.10; N, 10.31 Found: C, 70.40; H, 7.21; N, 10.37

A THF solution (25 mL) of the bis-amide (1.56 g, 3.8 mmol) was stirred under nitrogen at 0° C. and treated with the dropwise addition of a IM solution of lithium aluminium hydride in THF (38 mL, 10 equivalents). Once addition was complete, the reaction mixture was refluxed for 16 hours. After cooling to 0° C., the excess hydride reagent was destroyed by the addition of a saturated ammonium chloride solution, the mixture was filtered and the filtrate washed with ethyl acetate (50 mL). The organic solution was washed with water (2×50 mL), brine (50 mL) and dried over anhydrous sodium sulfate. Filtration and concentration gave the amine which was treated with ethereal HBr to afford the salt of the titled compound as a yellow colored solid (0.67 g).

$M^+$=379

Elemental Analysis for: $C_{24}H_{33}N_3O$ 2.0HBr $1.25H_2O$ Calculated: C, 51.12; H, 6.70; N, 7.45 Found: C, 50.72; H, 6.31; N, 7.34

Example 6

1-(2-Methoxy-phenyl)-4-piperidin-3-ylmethyl-piperazine

A solution of the amide from intermediate 4 (7.4 g, 21.8 mmol) and triethylamine (6 mL) in THF (100 mL) was treated with the dropwise addition of borane-THF (1.0 M, 76 mL) at 0° C. under nitrogen. The mixture was refluxed for 16 hours and after cooling to 0° C., the reaction was terminated by the addition of 2N-HCl (50 mL). After stirring for 1 hour, the solution was made basic with NaOH and the product extracted into ethyl acetate (3×35 mL). The combined organics were washed with water (50 mL), brine (50 mL) and dried over anhydrous sodium sulfate. Filtration and concentration in vacuum gave the required product (4.6 g, 81% yield). An ethanolic solution of the product was treated with a hot ethanolic solution of fumaric acid (1.0 equivalents) and afforded the fumarate salt of 1-(2-Methoxy-phenyl)-4-piperidin-3-ylmethyl-piperazine as a light yellow colored solid.

$M^+=289$

Elemental Analysis for: $C_{17}H_{27}N_3O$ $1.0C_4H_4O_4$ $2.0H_2O$ Calculated: C, 57.13; H, 7.99; N, 9.52 Found: C, 57.09; H, 7.84; N, 9.97

Example 7

Cyclohexyl-{3-[4-(2-methoxy-phenyl)-piperazin-1-ylmethyl]-piperidin-1-yl}-methanone Cyclohexanecarbonyl chloride (0.506 g, 3.5 mmol) was added to a solution of 1-(2-methoxyphenyl)-4-piperidin-3-ylmethyl-piperazine (1.0 g, 3.5 mmol) from example 6 and triethylamine (2 equivalents, 1 mL) in $CH_2Cl_2$ (30 mL) and the solution stirred under $N_2$ at 0° C. for 16 hours. The mixture was concentrated under vacuum, water (50 mL) added and the product extracted into ethyl acetate (3×25 mL). The combined organics were washed with water (25 mL), saturated sodium bicarbonate (20 mL) and brine (25 mL). After drying over sodium sulfate, filtration and concentration under vacuum afforded the titled product (1.13 g, 81% yield). An ethanolic solution of the product was treated with a hot ethanolic solution of fumaric acid (1.0 equivalents) and afforded the fumarate salt of the titled compound as a light yellow colored solid.

$M^+=399$

Elemental Analysis for: $C_{24}H_{37}N_3O_2$ $1.0C_4H_4O_4$ Calculated: C, 65.22; H, 8.01; N, 8.15 Found: C, 65.35; H, 8.23; N, 8.01

Example 8

{3-[4-(2-Methoxy-phenyl)-piperazin-1-ylmethyl]-piperidin-1-yl}-phenyl-methanone

Benzoyl chloride (0.49 g, 3.5 mmol) was added to a solution of 1-(2-methoxyphenyl)-4-piperidin-3-ylmethyl-piperazine (1.0 g, 3.5 mmol) from example 6 and triethylamine (2 equivalents, 1 mL) in $CH_2Cl_2$ (30 mL) and the solution stirred under $N_2$ at 0° C. for 16 hours. The mixture was concentrated under vacuum, water (50(mL) added and the product extracted into ethyl acetate (3×25 mL). The combined organics were washed with water (25 mL), saturated sodium bicarbonate (20 mL) and brine (25 mL). After drying over sodium sulfate, filtration and concentration under vacuum afforded the titled product (1.08 g, 79% yield). An ethanolic solution of the product was treated with a hot ethanolic solution of fumaric acid (1.0 equivalents) and afforded the fumarate salt of the titled compound as a light yellow colored solid.

$M^+=393$

Elemental Analysis for: $C_{24}H_{31}N_3O_2 0.75C_4H_4O_4$ Calculated: C, 67.48; H, 7.13; N, 8.74 Found: C, 67.76; H, 7.11; N, 8.88

Example 9

1-(1-Benzyl-piperidin-3-ylmethyl)-4-(2-methoxy-phenyl)-piperazine

Borane-THF (1.0M, 5 mmol) was added dropwise to a THF solution (8 mL) of {3-[4-(2-methoxyphenyl)-piperazin-1-ylmethyl]-piperidin-1-yl}-phenyl-methanone (0.54 g, 1.37 mmol) from example 8 at 0° C. under nitrogen. The mixture was refluxed for 16 hours and after cooling to 0° C., the reaction was terminated by the addition of 2N-HCl (50 mL). After stirring for 1 hour, the solution was made basic with NaOH and the product extracted into ethyl acetate (3×35 mL). The combined organics were washed with water (50(mL), brine (50(mL) and dried over anhydrous sodium sulfate. Filtration and concentration in vacuum gave the required product (0.36 g, 69% yield). An ethanolic solution of the product was treated with a hot ethanolic solution of fumaric acid (2.0 equivalents) and afforded the fumarate salt of the titled compound as a light yellow colored solid.

$M^+=379$

Elemental Analysis for: $C_{24}H_{33}N_3O$ $1.0C_4H_4O_4$ $1H_2O$ Calculated: C, 64.91; H, 7.69; N, 8.11 Found: C, 64.70; H, 7.37; N, 8.06

Example 10

3-(2-{3-[4-(2-Methoxy-phenyl)-piperazin-1-ylmethyl]-piperidin-1-yl}-ethyl)-1H-indole A mixture of 1-(2-methoxy-phenyl)-4-piperidin-3-ylmethyl-piperazine (0.5 g, 1.72 mmol) from example 6, 3-(2-bromoethyl)indole (0.38 g, 1 equivalent) and potassium carbonate (0.48 g, 2 equivalents) in acetonitrile (25 mL) were refluxed for 24 hours under a nitrogen atmosphere. Water (100 mL)) was added and the product extracted into ethyl acetate (3×50 mL). The combined organics were washed with water (25 mL), brine (25 mL) and dried over anhydrous sodium sulfate. Filtration and concentration in vacuum afforded the required product. Treatment with excess ethereal HCl gave the hydrochloride salt of the above titled compound as a white solid.

$M^+=432$

Elemental Analysis for: $C_{27}H_{36}N_4O$ $2.0HCl$ $1H_2O$ Calculated: C, 61.94; H, 7.70; N, 10.70 Found: C, 61.82; H, 7.41; N, 10.36

Example 11

[4-(1H-Indol-4-yl)-piperazin-1-yl]-piperidin-4-yl-methanone 4-(Indol-4-yl)piperazine (1.75 g, 8.7 mmol) was added to a mixture of DAEC (1.67 g, 1 equivalent), HOBT (1.3 equivalents, 1.53 g,) and N-butoxycarbonylisonipecotic acid (2 g, 8.7 mmol) in DMF (15 mL), and the resulting solution was treated with NMM (1.5 equivalents, 1.5 mL) and stirred at 0° C. for 16 hours. Water (100 mL) was added, the product extracted into ethyl acetate (3×50 mL) and the combined organics were washed with 1N-HCl (20 mL), saturated $NaHCO_3$ (25 mL) and dried over anhydrous sodium sulfate. Filtration and concentration in vacuum afforded the product as a white solid (3.07 g, 85% yield). A sample of the carbamate (1.5 g, 3.63 mmol) was dissolved in 4M-HCl dioxan (20 mL) and the solution stirred at ambient temperature for 4 hours. The mixture was concentrated in vacuum, diethyl ether (50 mL) added and the precipitated product collected by filtration and washed with ether (50 mL) to afford a tan colored solid (1.2 g, 98% yield)

m.p.>240° C.

$M^+=313$

Elemental Analysis for: $C_{18}H_{24}N_4O$ $2HCl1$ Calculated: C, 56. 10; H, 6.80; N, 14.54 Found: C, 55.76; H, 6.65; N, 14.11

Example 12

4-[4-(1-Methyl-piperidin-4-ylmethyl)-piperazin-1-yl]- 1H-indole

Under a nitrogen atmosphere, a sample of the carbamate (1.5 g, 3.63 mmol) from example 11 in THF (20 mL) was treated with the dropwise addition of 1.0M lithium aluminium hydride in THF (35 mL, 10 equivalents) at 0° C. and the solution refluxed for 16 hours. After cooling to ambient temperature, the excess hydride was destroyed by the addition of ammonium chloride solution and the mixture filtered. Ethyl acetate (50 mL) was added, the solution washed with water (50 mL), brine (25 mL) and dried over anhydrous sodium sulfate. Filtration and concentration gave the titled product, which was converted to its hydrochloride salt by the action of ethereal-HCl.

$M^+=312$

Elemental Analysis for: $C_{19}H_{28}N_4$ 1HCl $0.5H_2O$ Calculated: C, 63.76; H. 8.45; N, 15.65 Found: C, 63.96; H, 8.31; N, 15.43

Compounds of the present invention bind with very high affinity to the 5-HT1A receptor and consequently, they are useful for the treatment of central nervous system disorders such as depression, anxiety, sleep disorders, sexual dysfunction, alcohol and cocaine addiction, cognition enhancement and related problems in addition to the treatment of Alzheimer's disease, Parkinson's disease, obesity and migraine.

5-HT1A Receptor Binding Assay

High affinity for the serotonin $5-HT_{1A}$ receptor was established by testing the claimed compound's ability to displace [$^3$H] 8-OH-DPAT binding in CHO cells stably transfected with the human 5HT1A receptor. Stably transfected CHO cells are grown in DMEM containing 10% heat inactivated FBS and non-essential amino acids. Cells are scraped off the plate, transferred to centrifuge tubes, and washed twice by centrifugation (2000 rpm for 10 min., 4° C.) in buffer (50 mM Tris pH 7.5). The resulting pellets are aliquoted and placed at −80° C. On the day of assay, the cells are thawed on ice and resuspended in buffer. The binding assay is performed in a 96 well microtiter plate in a total volume of 250 μL. Non-specific binding is determined in the presence of 10 mM 5-HT, final ligand concentration is 1.5 nM. Following a 30 minute incubation at room temperature, the reaction is terminated by the addition of ice cold buffer and rapid filtration through a GF/B filter presoaked for 30 minutes in 0.5% PEI. Compounds are initially tested in a single point assay to determine percent inhibition at 1, 0.1, and 0.01 mM, and Ki values are determined for the active compounds.

5-HT1A Receptor Intrinsic Activity Assay

The intrinsic activity of compounds of the present invention was established by testing the claimed compounds ability to reverse the stimulation of cyclic adenosinemonophosphate (cAMP) in CHO cells stably transfected with the human 5HT1A receptor.

Stably transfected CHO cells were grown in DMEM containing 10% heat inactivated FBS and non-essential amino acids. The cells are plated at a density of $x10^6$ cells per well in a 24 well plate and incubated for 2 days in a $CO_2$ incubator. On the second day, the media is replaced with 0.5 mL treatment buffer (DMEM+25 mM HEPES, 5 mM theophylline, 10 μM pargyline) and incubated for 10 minutes at 37° C. Wells are treated with forskolin (1 μM final concentration) followed immediately by the test compound (0.1 and 1 μM for initial screen) and incubated for an additional 10 minutes at 37° C. The reaction is terminated by removal of the media and addition of 0.5 mL ice cold assay buffer (supplied in the RIA kit). Plates are stored at −20° C. prior to assessment of cAMP formation by RIA. $EC_{50}$), values are determined for the active test compounds. Compounds shown to have no agonist activities (Emax=0%) are further analyzed for their ability to reverse agonist induced activity. In separate experiments. 6 concentrations of antagonist are preincubated for 20 minutes prior to the addition of agonist and forskolin. Cells are harvested as described above. The cAMP kit is supplied by Amersham and the RIA is performed as per kit instructions, and calculations of $IC_{50}$ performed by GraphPad Prism.

| Compound | 5-HT1A binding Ki (nM) | cAMP Emax |
|---|---|---|
| Example 1 | TBD | 0% |
| Example 3 | 8.4 | 89% |
| Example 6 | 2.0 | 0% |
| Example 9 | 14 | 79% |

Hence, compounds of the present invention exhibit high affinity for the 5HT1A receptor subtype and exhibit intrinsic activity as evidenced by their ability to reverse stimulation of cyclic adenosinemonophosphate (cAMP). Accordingly, compounds of the present invention are useful for treatment of disorders of the central nervous system and may be administered to a patient suffering from one or more of said disorders. Treatment, as used herein, refers to the alleviation or amelioration of symptoms of a particular disorder in a patient. In addition, compounds of the present invention may be administered as part of a treatment regime that includes other agents which act on the central nervous system. In some preferred embodiments, compounds of the present invention are part of a combination therapy including a serotonin reuptake inhibitor. Serotonin reuptake inhibitors useful in combination therapies of the present invention fluoxetine, fluvoxamine, paroxetine, sertraline and venlafaxine. Said agents may be administered at the same time, where they may be combined into a single dosage form, or at a different time, as compounds of the present invention, while still being part of the regime of the combination therapy.

Compounds of the invention may be administered to a patient either neat or with a convention pharmaceutical carrier.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The therapeutically effective dosage to be used in the treatment of a specific psychosis must be subjectively determined by the attending physician. The variables involved include the specific psychosis or state of anxiety and the size, age and response pattern of the patient. The novel method of the invention for treating conditions related to or are affected by the 5-HT1A receptor comprise administering to warm-blooded animals, including humans, an effective amount of at least one compound of Formula A and its non-toxic, pharmaceutically acceptable addition salts. The compounds may be administered orally, rectally, parenterally or topically to the skin and mucosa. The usual daily dose is depending on the specific compound, method of treatment and condition treated. The usual daily dose is 0.01–1000 mg/Kg for oral application, preferably 0.5–500 mg/Kg, and 0.1–1000 mg/Kg for parenteral application, preferably 0.5–50 mg/Kg.

What is claimed is:

1. A compound of formula (A),

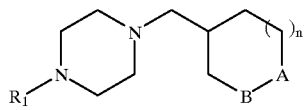

in which:
R1 is phenyl; 2-, 3- or 4-pyridyl; 2-pyrimidyl; benzodioxan-5-yl; indol-4-yl; 3-thienyl: 1-, or 2-naphthyl;
A is $NR_2$ and B is $CH_2$;
$R_2$ is hydrogen, alkyl, cycloalkyl, alkylcycloalkyl, heterocycloalkyl, alkylhetero-cycloalkyl, aryl, aralkyl, alkylheteroaryl, or $COR_3$;
$R_3$ is hydrogen, alkyl, cycloalkyl, heterocycloalkyl, aryl, or heteroaryl;

n is an integer from 0 to 2, or a pharmaceutical salt thereof.

2. A compound of claim 1 wherein R1 is phenyl or indol-4-yl.

3. A compound of claim 1 wherein R2 is aralkyl, alkylcycloalkyl, alkylheteroaryl, alkylheterocycloalkyl or COR3.

4. A compound of claim 1 wherein R1 is phenyl or indol-4-yl, R2 is COR3 and R3 is cyclohexyl, phenyl or piperadin-4-yl.

5. A compound of formula (A),

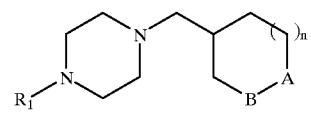

in which:
$R_1$ is aryl or heteroaryl;
A is $CH_2$ and B is $NR_2$;
$R_2$ is hydrogen, alkyl, cycloalkyl, alkylcycloalkyl, heterocycloalkyl, alkylhetero-cycloalkyl, aryl, aralkyl, heteroaryl, alkylheteroaryl, or $COR_3$;
$R_3$ is hydrogen, alkyl, cycloalkyl, heterocycloalkyl, aryl, or heteroaryl;
n is an integer from 0 to 2, or a pharmaceutical salt thereof.

6. A compound selected from the group consisting of
1-(2-Methoxy-phenyl)-4-piperidin-4-ylmethyl-piperazine,
Cyclohexyl- {4-[4-(2-methoxy-phenyl)-piperazin-1-ylmethyl]-piperidin-1-yl}-methanone,
1- (1-Cyclohexylmethyl-piperidin-3-ylmethyl)-4-(2-methoxy-phenyl)-piperazine,
{4-[4-(2-Methoxy-phenyl)-piperazin-1-ylmethyl]-piperidin-1-yl}-phenyl-methanone,
1-(1-Benzyl-piperidin-4-ylmethyl)-4-(2-methoxy-phenyl)-piperazine,
1-(2-Methoxy-phenyl)-4-piperidin-3-ylmethyl-piperazine,
Cyclohexyl- {3-[4-(2-methoxy-phenyl)-piperazin-1-ylmethyl]-piperidin-1-yl}-methanone,
{3-[4-(2-Methoxy-phenyl)-piperazin-1-ylmethyl]-piperidin-1-yl}-phenyl-methanone,
1-(1-Benzyl-piperidin-3-ylmethyl)-4-(2-methoxy-phenyl)-piperazine,
3-(2-{3-[4-(2-Methoxy-phenyl)-piperazin-1-ylmethyl]-piperidin-1-yl}-ethyl)-1H-indole,
[4-(1 H-Indol-4-yl)-piperazin-1-yl]-piperidin-4-yl-methanone,
4-[4-(1-Methyl- piperidin-4-ylmethyl)-piperazin-1-yl]-1H-indole, or pharmaceutical salts thereof.

7. A compound of claim 5 wherein $R_1$ is phenyl; 2-, 3- or 4-pyridyl; 2-pyrimidyl; benzodioxan-5-yl; indol-4-yl; 3-thienyl; 1-, or 2-naphthyl.

8. A compound of claims 5 wherein $R_1$ is phenyl or indol-4-yl.

9. A compound of claims 5 wherein $R_2$ is aralkyl, alkylcycloalkyl, alkylheteroaryl, alkylheterocycloalkyl or $COR_3$.

10. A compound of claim 5 wherein $R_1$ is phenyl or indol-4-yl, $R_2$ is CO $R_3$ and $R_3$ is cyclohexyl, phenyl or piperadin-4-yl.

11. A pharmaceutical composition comprising a therapeutically effective amount of a compound of formula (A),

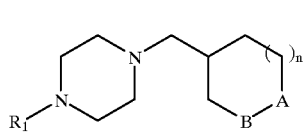

in which:
R₁ is phenyl: 2-, 3- or 4-pyridyl; 2-pyrimidyl; benzodioxan-5-yl; indol-4-yl; 3-thienyl; I-, or 2-naphthyl;
A is NR₂ and B is CH₂;
R₂ is hydrogen, alkyl, cycloalkyl, alkylcycloalkyl, heterocycloalkyl, alkylhetero-cycloalkyl, aryl, aralkyl, heteroaryl, alkylheteroaryl, or COR₃;
R₃ is hydrogen, alkyl, cycloalkyl, heterocycloalkyl, aryl, or heteroaryl;
n is an integer from 0 to 2, or a pharmaceutical salt thereof, and a pharmaceutically acceptable carrier or excipient.

12. A pharmaceutical composition comprising a therapeutically effective amount of a compound of formula (A),

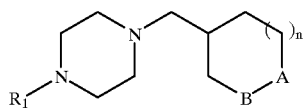

in which:
R₁ is aryl or heteroaryl;
A is CH2 and B is NR₂;
R₂ is hydrogen, alkyl, cycloalkyl, alkylcycloalkyl, heterocycloalkyl, alkylhetero-cycloalkyl, aryl, aralkyl, heteroaryl, alkylheteroaryl, or COR₃;
R₃ is hydrogen, alkyl, cycloalkyl, heterocycloalkyl, aryl, or heteroaryl;
n is an integer from 0 to 2, or a pharmaceutical salt thereof, and a pharmaceutically acceptable carrier or adjuvant.

13. A method of treating a patient suffering from a disorder of the central nervous system associated with the 5-hydroxytryptamine 1A receptor subtype selected from the group consisting of depression, anxiety, panic, sleep disorders, sexual dysfunction, migraine or obesity, comprising providing to said patient a therapeutically effective amount of a compound of Formula A,

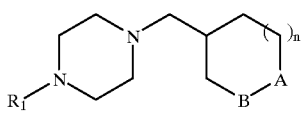

in which:
R₁ is phenyl; 2-, 3- or 4-pyridyl; 2-pyrimidyl; benzodioxan-5-yl; indol-4-yl; 3-thienyl; 1-, or 2-naphthyl;
A is NR₂ and B isCH₂;
R₂ is hydrogen, alkyl, cycloalkyl, alkylcycloalkyl, heterocycloalkyl, alkylhetero-cycloalkyl, aryl, aralkyl, alkylheteroaryl, or COR₃;
R₃ is hydrogen, alkyl, cycloalkyl, heterocycloalkyl, aryl, or heteroaryl;
n is an integer from 0 to 2, or a pharmaceutical salt thereof.

14. A method of treating a patient suffering from a disorder of the central nervous system associated with the 5-hydroxytryptamine 1A receptor subtype selected from the group consisting of depression, anxiety, panic, sleep disorders, sexual dysfunction, migraine or obesity, comprising providing to said patient a therapeutically effective amount of a compound of Formula A,

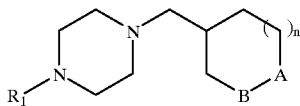

in which:
R₁ is aryl or heteroaryl;
A is CH₂ and B is NR₂;
R₂ is hydrogen, alkyl, cycloalkyl, alkylcycloalkyl, heterocycloalkyl, alkylhetero-cycloalkyl, aryl, aralkyl, heteroaryl, alkylheteroaryl, or COR₃;
R₃ is hydrogen, alkyl, cycloalkyl, heterocycloalkyl, aryl, or heteroaryl;
n is an integer from 0 to 2, or a pharmaceutical salt thereof.

* * * * *